United States Patent
Mark et al.

(10) Patent No.: US 10,828,123 B2
(45) Date of Patent: Nov. 10, 2020

(54) NAVIGATION STYLET FOR A TISSUE ACCESS SYSTEM

(71) Applicant: Nico Corporation, Indianapolis, IN (US)

(72) Inventors: Joseph L. Mark, Indianapolis, IN (US); Brian C. Dougherty, Terre Haute, IN (US)

(73) Assignee: Nico Corporation, Indianapolis, IN (US)

( * ) Notice: Subject to any disclaimer, the term of this patent is extended or adjusted under 35 U.S.C. 154(b) by 632 days.

(21) Appl. No.: 15/198,780

(22) Filed: Jun. 30, 2016

(65) Prior Publication Data

US 2017/0000579 A1   Jan. 5, 2017

Related U.S. Application Data

(60) Provisional application No. 62/188,180, filed on Jul. 2, 2015.

(51) Int. Cl.
| | | |
|---|---|---|
| *A61B 90/11* | (2016.01) | |
| *A61B 17/34* | (2006.01) | |
| *A61B 90/10* | (2016.01) | |
| *A61B 34/20* | (2016.01) | |
| *A61B 90/00* | (2016.01) | |

(52) U.S. Cl.
CPC .......... *A61B 90/11* (2016.02); *A61B 17/3417* (2013.01); *A61B 17/3421* (2013.01); *A61B 2034/2072* (2016.02); *A61B 2090/0813* (2016.02); *A61B 2090/103* (2016.02); *A61B 2090/3983* (2016.02)

(58) Field of Classification Search
CPC . A61B 90/11; A61B 17/3421; A61B 17/3417; A61B 2090/0813; A61B 2090/103; A61B 5/061; A61B 2090/0811; A61B 2090/0807; A61B 2034/2051; A61B 8/0841
See application file for complete search history.

(56) References Cited

U.S. PATENT DOCUMENTS

| | | | | |
|---|---|---|---|---|
| 8,080,000 | B2 * | 12/2011 | Makower | A61B 1/00135 604/510 |
| 8,864,787 | B2 * | 10/2014 | Muni | A61B 17/24 424/434 |
| 2001/0034530 | A1 * | 10/2001 | Malackowski | A61B 34/20 606/130 |
| 2007/0283773 | A1 * | 12/2007 | Baldewein | A61B 5/0031 73/866.5 |
| 2012/0071748 | A1 * | 3/2012 | Mark | A61B 17/32001 600/411 |

* cited by examiner

*Primary Examiner* — Tuan V Nguyen
*Assistant Examiner* — Chima U Igboko
(74) *Attorney, Agent, or Firm* — Kristin L. Murphy; Honigman LLP

(57) ABSTRACT

A navigation stylet assembly is disclosed. The navigation stylet comprises a navigation element, a handle, and an attachment member configured to be attached to a navigation array. The handle is attached to the navigation element, and the navigation element is partially disposed within the handle and exits the handle so as to be oriented at an angle that extends away from a central axis disposed through a body element of the navigation element.

19 Claims, 14 Drawing Sheets

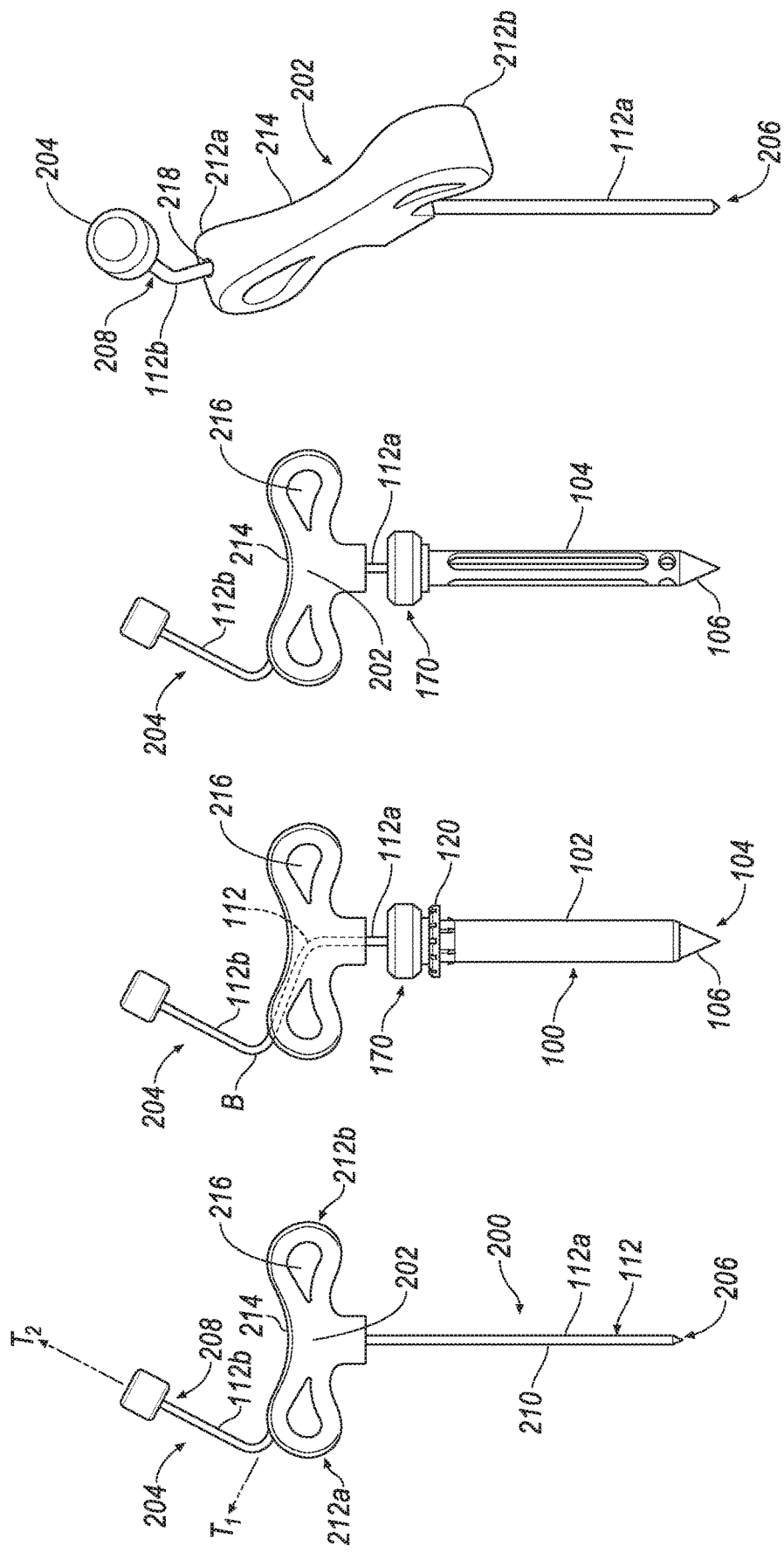

NAVIGATION STYLET FOR A TISSUE ACCESS SYSTEM

TECHNICAL FIELD

The present disclosure relates to a navigation stylet for a tissue access system that cooperates with a navigation system.

BACKGROUND

Diagnosis and treatment of conditions affecting the brain are among the most difficult and complex problems that face the medical profession. The brain is a complex and delicate soft multi-component tissue structure that receives multiple inputs, processes these inputs, responds to the inputs and controls bodily functions through a complex neural network connected to the rest of the body through the spinal cord. The brain and spinal cord are contained within and protected by significant bony structures, e.g., the skull and the spine. Given the difficulty of safely accessing areas of the brain housed within the hard bony protective skull, and the delicate network and complex interactions that form the neural communication network contained within the brain, the internal corridor within the brain, that define the human body's ability to carry on its functions of speech, sight, hearing, functional mobility, reasoning, emotions, respiration and other metabolic functions, the diagnosis and treatment of brain disorders presents unique challenges not encountered elsewhere in the body.

For example, abnormalities such as intracranial cerebral hematomas (ICH), abscesses, glioblastomas (GB), metastases (mets) and functional diseases manifest themselves in the intraparenchymal subcortical space (i.e., the white matter) of the brain are particularly challenging to access, let alone treat. The white matter and the cortex contain eloquent communication structures (neural network) which are located in the subcortical space, called fiber tracts and fascicles which make up the fascicular anatomy. Thus, traditionally, unless the ICH, GB, and/or mets were considered anything but "superficial," such conditions have been considered challenging to access or inoperable, simply because getting to the abnormality ICH, GB and/or mets are considered just as damaging as letting the condition take its course. Similarly, tissue abnormalities such as tumors, cysts and fibrous membrane growths which manifest within the intraventricular space of the brain are considered challenging to safely access and often inoperable, due to their locations within the brain and the eloquent real estate that must be traversed to access them.

In order to assist in diagnosis and subsequent treatment of brain disorders, clear, accurate imaging of brain tissue through the skull is required. In recent years significant advances have been made in imaging technology, including stereotactic X-ray imaging, Computerized Axial Tomography (CAT), Computerized Tomographic Angiography (CTA), Position Emission Tomography (PET) and Magnetic Resonance Imaging (MRI) sequences such as Diffusion Tensor Imaging (DTI) and Diffusion Weighted Images (DWI). Navigation systems (instrument position tracking systems) have also been improved to allow for the input of many of these improved imaging sequences such as CT and MRI to allow for improved accuracy when tracking instruments within the human body with the information downloaded to the navigational system from these imaging system sequences. These imaging devices and techniques permit the surgeon to observe conditions within the brain in a non-invasive manner without opening the skull, as well as provide a map of critical structures surrounding an area of interest, including structures such as blood vessels, membranes, tumor margins, cranial nerves, including the fascicular anatomy. If an abnormality is identified through the use of one or more imaging modalities and/or techniques, it may be necessary or desirable to biopsy or remove the abnormality. The navigational system allows for the intraoperative translation of these sequences during a procedure so that the user may maintain their intraoperative location and orientation during the procedure.

Once a course of action has been determined based upon one or more imaging techniques, a surgical treatment may be necessary or desired. In order to operate surgically on the brain, access must be obtained through the skull and eloquent brain tissue containing blood vessels and nerves that can be adversely affected by even slight disturbances. Therefore, great care must be taken when traversing the internal corridor and operating on the brain so as not to disturb delicate blood vessels and nerves to prevent adverse consequences resulting from a surgical intervention.

Traditionally, accessing abnormalities which manifest in deeper spaces within the brain has meant a need for a surgery that creates a highly invasive approach. In some instances, in order to obtain access to target tissue, a substantial portion of the skull is removed and entire sections of the brain are retracted or even removed to obtain access to deliver optics, light and instrumentation. For example, surgical brain retractors are used to pull apart or spread delicate brain tissue, which can leave pressure marks from lateral edges of the retractor. In some instances, a complication known as "retraction injury" may occur due to use of brain retractors. Of course, such techniques are not appropriate for all situations, and not all patients are able to tolerate and recover from such tissue disruptive invasive techniques.

It is also known to access certain portions of the brain by creating a burr hole craniotomy, but only limited surgical techniques may be performed through such smaller openings. In addition, some techniques have been developed to enter through the nasal passages, opening an access hole through the occipital bone to remove tumors located, for example, in the area of the pituitary, such as skull based tumors.

A significant advance in brain surgery is stereotactic surgery involving a stereotactic frame correlated to stereotactic X-ray images to guide a navigational system probe or other surgical instrument through an opening formed in the skull through brain tissue to a target lesion or other body. A related advance is frameless image guidance, in which an image of the surgical instrument is superimposed on a pre-operative image to demonstrate the location of the instrument to the surgeon and trajectory of further movement of the probe or instrument on or within the skull.

While minimally invasive and non-disruptive access systems have been developed to now provide access to previously difficult to access or what were previously considered inoperable areas in the brain and spine, many such access systems do not have the capability to provide navigational information during positioning of the access system. Nor can the navigational system be used simultaneously with the optical imaging system thereby allowing for intra-operatively, simultaneous use of both optical imaging viewing and navigational system location orientation viewing. For example, as shown in the prior art navigation probe assembly 500 depicted in FIG. 1, a navigational array 502 that is mounted on a proximal end of a probe body 504. However, when positioned within a surgical access system, the navigational array 502 will actually serve to block any optical imaging system, which are typically mounted above the operating field.

Notwithstanding the foregoing advances in navigational technology of both frame and frameless stereotactic image guidance techniques, there remains a need for improved instrumentation of these navigational systems which allow for the use of new advances in minimally invasive access systems.

BRIEF DESCRIPTION OF THE DRAWINGS

Exemplary embodiments of the present disclosure will now be described in greater detail with reference to the attached figures, in which:

FIG. 7 is a side elevational view of a first embodiment of a navigation stylet for use with an obturator element of a surgical access system;

FIG. 8 is a side elevational view of the navigation stylet of FIG. 7, assembled to a surgical access system;

FIG. 9 is a side elevational view of the navigation stylet of FIG. 7, assembled to a surgical access system with an outer sheath of the surgical access system of FIG. 8 removed;

FIG. 10 a top perspective view of the navigation stylet of FIG. 7;

DETAILED DESCRIPTION

Figure 1:
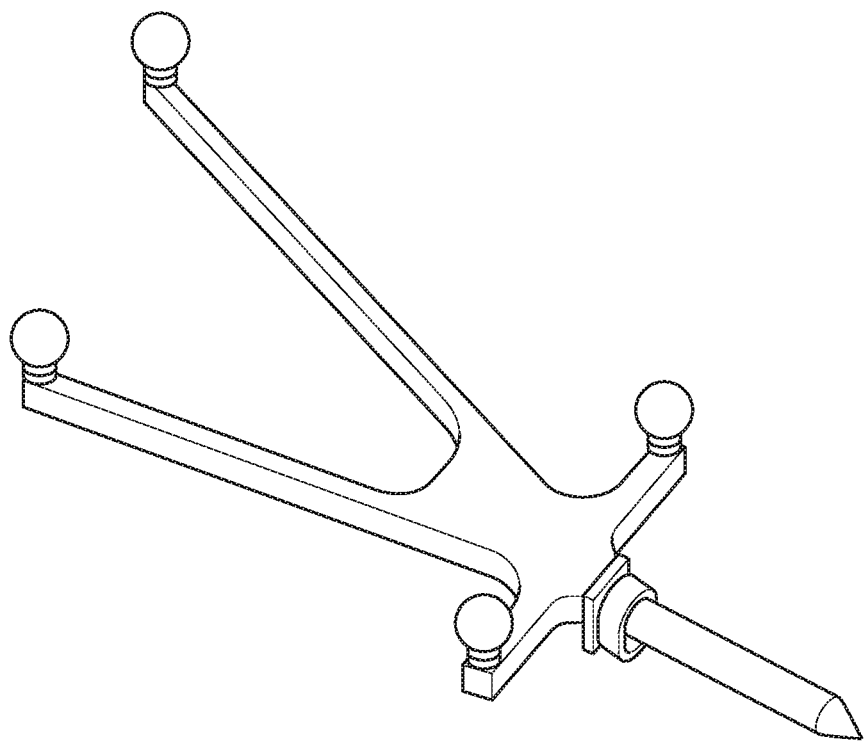
FIG. 1 is a perspective view of a prior art navigational probe.

Referring now to the discussion that follows and also to the drawings, illustrative approaches to the disclosed assemblies and methods are shown in detail. Although the drawings represent some possible approaches, the drawings are not necessarily to scale and certain features may be exaggerated, removed, or partially sectioned to better illustrate and explain the present disclosure. Further, the descriptions set forth herein are not intended to be exhaustive or otherwise limit or restrict the claims to the precise forms and configurations shown in the drawings and disclosed in the following detailed description.

Described herein is surgical access assembly, various components for use in same, and a method of using the surgical access assembly. The components disclosed herein provide surgeons with an enhanced ability to minimize trauma to the patient, while providing efficient improved minimally invasive surgical techniques, such as, for example, during intracranial surgical techniques. The components disclosed herein may further be used for application of targeted and effective treatment regimens. The surgical access assembly disclosed herein may include components similar to those shown in copending U.S. application Ser. No. 13/444,732, the contents of which are incorporated by reference in its entirety.

Figure 2:
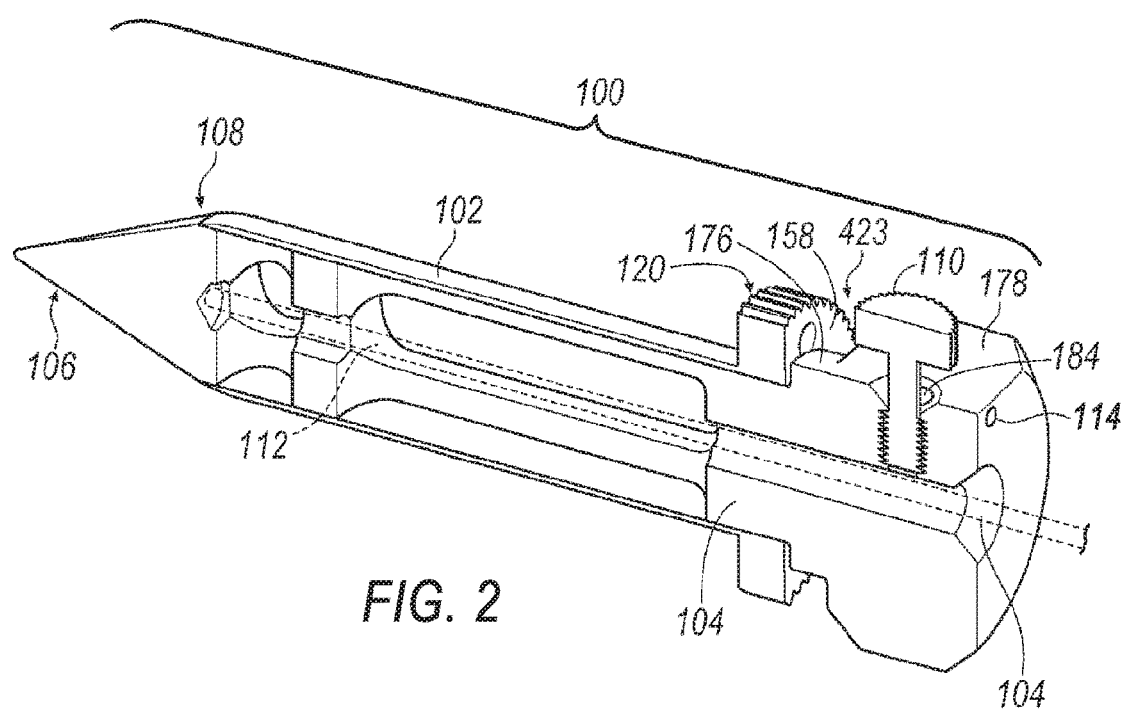
FIG. 2 is a perspective cross-sectional view of an exemplary arrangement of a surgical access assembly.

Referring to FIG. 2, a perspective cross-sectional view of a surgical access assembly 100 is shown. In one exemplary arrangement, surgical access assembly 100 comprises a hollow outer sheath 102 and a selectively removable obturator 104. As best seen in FIG. 2, obturator 104 is configured with a length that is longer than a length of outer sheath 102 such that a distal end 106 of obturator 104 protrudes a predetermined distance from a distal end 108 outer sheath 102, as will be discussed below in greater detail.

A locking member 110 may also be provided. Locking member 100 is configured to operatively retain a portion of a separate navigation member 112 (shown in phantom) within obturator 104, as will be discussed in greater detail below. A retaining member 114 may be secured within a portion of obturator 104 to prevent locking member 110 from being completely disengaged from obturator 104.

Figure 3A:
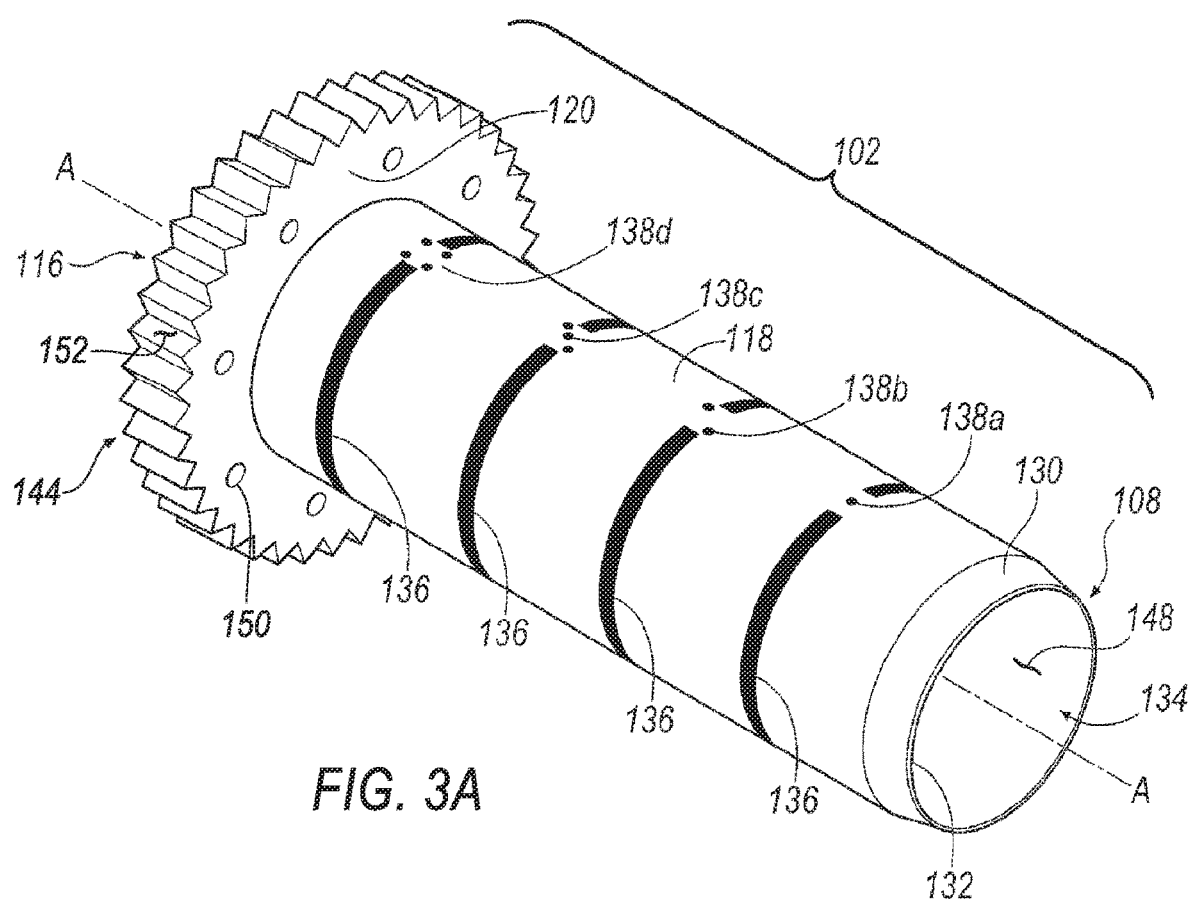
FIG. 3A is a perspective view of an outer sheath of the surgical access assembly of FIG. 2.

Referring now to FIG. 3, outer sheath 102 will be described in greater detail. Outer sheath 102 is defined by distal end 108 and a proximal end 116 and includes a generally hollow body portion 118 and a grip portion 120. In one exemplary arrangement, grip portion 120 is configured as a ring, as illustrated in the drawings. However, it is understood that grip portion 120 need not be configured as a ring and may have other shapes conducive for a user to grip. For ease of explanation, grip portion 120 will be referred to hereinafter as grip ring 120. Grip ring 120 is fixedly secured to body portion 118 at proximal end 116. In one exemplary arrangement, body portion 118 is constructed of a clear biocompatible material that permits viewing of normal tissue, abnormal tissue, as well as critical structures that are disposed outside of body portion 118 when outer sheath 102 is disposed within such tissue. In one exemplary arrangement, outer sheath 102 is constructed of polycarbonate, though other biocompatible materials may be employed, including resins.

Distal end 108 of outer sheath 102 may be configured with a tapered portion 130 that extends towards a center axis A-A of outer sheath 102 to a distal edge 132 that surrounds an opening 134 in distal end 108 of outer sheath 102. Tapered portion 130 serves to ease the transition between outer sheath 102 and a distal tip potion 172 of obturator 104, without drag, trauma or coring of tissue from a diameter that defines a body portion 168 of obturator 104 to a diameter that defines body portion 118 of outer sheath 102 when the obturator 104 is inserted within the outer sheath 102 in an introducing configuration. In one exemplary configuration, distal end 108 may be configured with a radius or other configuration so as to create a smooth/atraumatic transition of the brain tissue when surgical access assembly 100 is inserted into the brain in the introducing configuration.

For example, as best seen in FIG. 3, distal edge 132 is configured so as to be non-sharpened and radiused. In one exemplary arrangement, distal edge 132 is configured as a 0.3 mm diameter radiused rim. Tapered portion 130 and radiused distal tip 132 cooperate with obturator 104 to atraumatically move tissue, as well as various structures within the brain, including white matter, away from outer sheath 102 without cutting tissue or such structures.

Body portion 118 may further be provided with a plurality of spaced apart indicators 136. Indicators 136 generally extend about the circumference of body portion 118 and each may further incorporate a secondary indicator 138 that visually illustrates a predetermined location on body portion 118, as shown in FIG. 2. While FIG. 2 illustrates four indicators 136, it is understood that body portion 118 may be provided in a variety of lengths and that any number of indicators 136 may be provided. Body portion 118 may also be provided with a longitudinal indicator (not shown).

Indicators 136 and 138 may be printed onto either an internal or external surface of body portion 118 with an imaging visible ink such as, for example ink containing fluro-deoxyglucose (FDG), Technicium 99, Gadolinium, titanium dust, barium sulfate, a combination of the above or other suitable imaging material. Indicators 136 and 138 provide a reference point for the operator of system 100, as structures may be visible through body portion 118. Indicators 136 and 138 may also be configured to be visible under MRI, CT, PET, or any other suitable imaging modality to enable easy identification of areas of interest. In one alternative embodiment, indicators 136 and/or 138 may be etched or printed onto body portion 118, either on the internal or external surface of body portion 118.

Figure 3B:
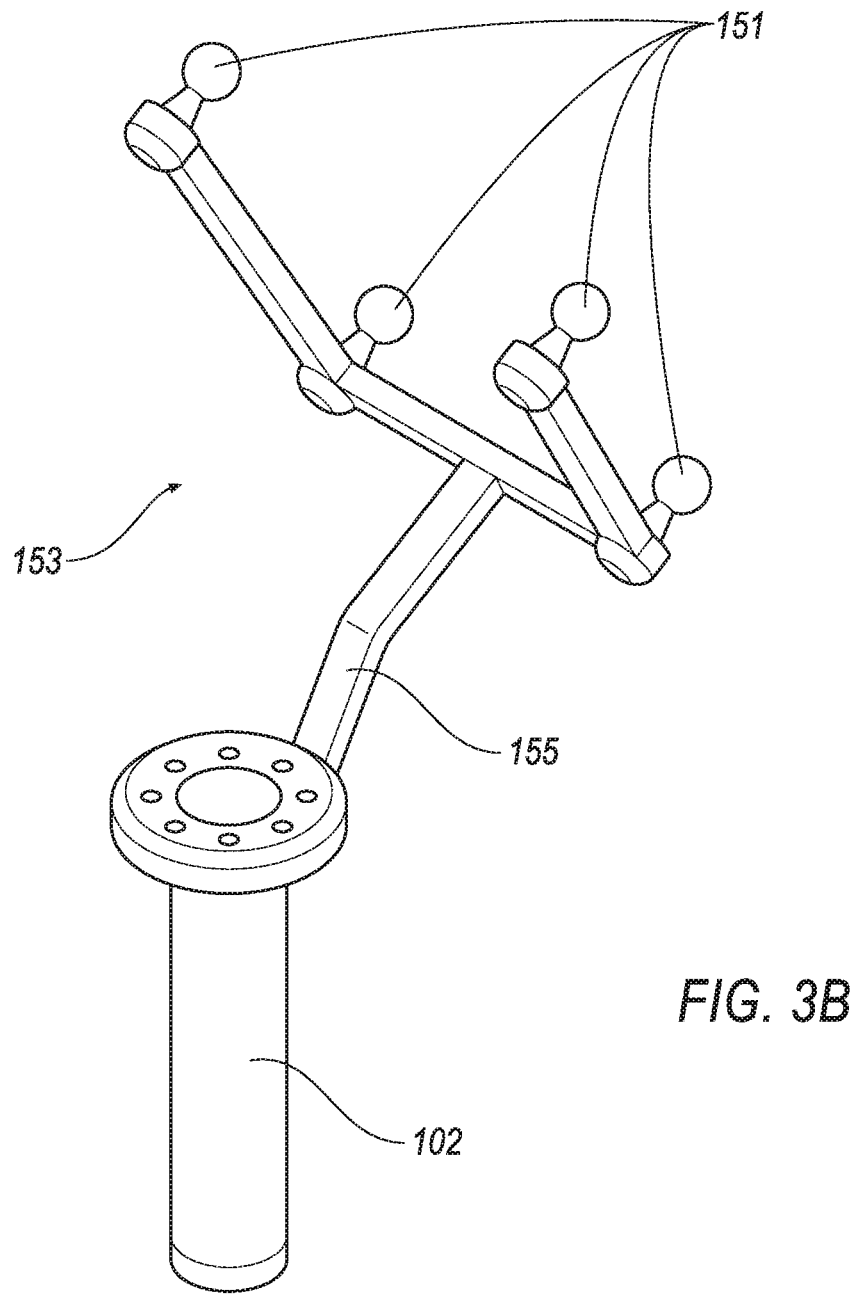
FIG. 3B is a perspective view of the outer sheath of FIG. 3A with a tracking member assembly mounted thereto.

In one exemplary arrangement, referring to FIG. 3B, the outer sheath 102 may include a plurality of tracking elements 151 as part of a tracking marker assembly 153. The tracking marker assembly 153 is comprised of a rigid structure 155 to support the attachment of a plurality of tracking elements 151. The tracking elements 151 may be of any suitable form to enable tracking as described below. In some embodiments, assembly 153 may be selectively attached to outer sheath 102, or integral with outer sheath 102. It is to be understood that the orientation of the tracking elements 151 may be selected to provide suitable tracking over a wide range of relative medical instrument positional orientations and poses, and relative imaging sensor positional orientations and poses.

In one exemplary arrangement, the tracking elements 151 may be used to determine spatial positioning of the medical instruments within a patient. More specifically, tracking elements 151 that could be used would be RF, EM, LED (pulsed and un-pulsed), glass spheres, reflective stickers, unique structures and patterns, where the RF and EM may have specific signatures for the specific tools they would be attached to. The reflective stickers, structures and patterns, glass spheres, and LEDs could all be detected using optical detectors, while RF and EM could be picked up using antennas. Advantages to using EM and RF tags would include removal of the line of sight condition during the operation, where using optical system removes the additional noise from electrical emission and detection systems.

In a further embodiment, printed or 3-D design markers could be used for detection by an imaging sensor provided it has a field of view inclusive of the tracked medical instruments. The printed markers could also be used as a calibration pattern to provide (3-D) distance information to the imaging sensor. These identification markers may include designs such as concentric circles with different ring spacing, and/or different types of bar codes. In an additional embodiment, reflective spheres, or other suitable active or passive tracking markers, may be oriented in multiple planes to expand the range of orientations that would be visible to a camera for the imaging system. An example of a tracking marker assembly 153 is shown in published U.S. patent application US20160113728, the contents of which are incorporated herein by reference.

Other tracking configurations are also contemplated. For example, a light ring or a support ring may be disposed around the grip ring 120 with flange members that support reflective balls or other sensors that may be configurable to cooperate with a navigation system, to indicate the location of outer sheath 102 after insertion into an area of interest, as described in U.S. Pat. No. 9,265,523, the contents of which are incorporated by reference in its entirety.

Grip ring 120 is generally configured as a flange member defined by an outer periphery 144 and an inner opening. The inner opening may be sized to generally correspond to the diameter of a lumen 148 (see FIG. 2) defined by body portion 118. The outer periphery of grip ring 120 is sized to have a diameter that is larger than lumen 148 of body portion 118. The flange member may further be provided with one or more small openings 150 that are disposed therein. In one exemplary arrangement, a plurality of small openings 150 are provided that are spaced generally equi-distantly about the inner opening of the grip ring 120. Outer periphery 144 may further be provided with a textured surface 152 to provide for ease of gripping outer sheath 102. For example, in one exemplary arrangement, textured surface 152 comprises a plurality of alternating ridges and grooves. However, it is understood that other textured surfaces may be employed.

Referring to FIGS. 4A-6C, obturator 104 will now be described. Obturator 104 is defined by distal end 106, a proximal end 166, a body portion 168 and a handle portion 170. Distal end 106 is configured with a generally conical shaped distal tip portion 172 that tapers to a tip member 174 to provide atraumatic dilation of tissue. In one exemplary arrangement, tip portion 172 tapers toward a closed tip member 174 so as to prevent coring of tissue as obturator 104 is inserted into the brain.

There are a number of variables that play the selection of the angle a that defines the taper of tip portion 172. These variables include the size of an outer diameter D1 of obturator 104, the desired length that distal tip portion 172 extends from body portion 168, and the desired offset for a distal tip of navigation member 112 and tip member 174. More specifically, it is contemplated that surgical access assembly 100 will be provided as part of a kit that may include multiple sized outer sheaths 102 and obturators 104, to provide the surgeon with a choice of different diameter sizes and lengths so as to provide flexibility for accessing areas of interest within the brain. However, to insure that the distal tip 174 is determinable regardless of which size diameter D1 of obturator 104 is used, taper angle a may be selectively adjusted. For embodiments that utilize navigation member 112 that positions a distal end thereof at a set position within obturator 104 (as will be explained in further detail below), to maintain an identical offset length between the distal end of navigation member 112 and distal tip 174 in different diameter D1 sized obturators 104, taper angle a will need to be increased, as diameter D1 increases.

For example, if diameter D1 of obturator 104 is 13.5 mm, an exemplary angle a may be 45.5° to provide effective atraumatic dilation, as well as a determinable distal tip 174 location. However, if diameter D1 of obturator 104 is 15.5 mm, an exemplary angle α' may be 52.8°.

Figure 5A:
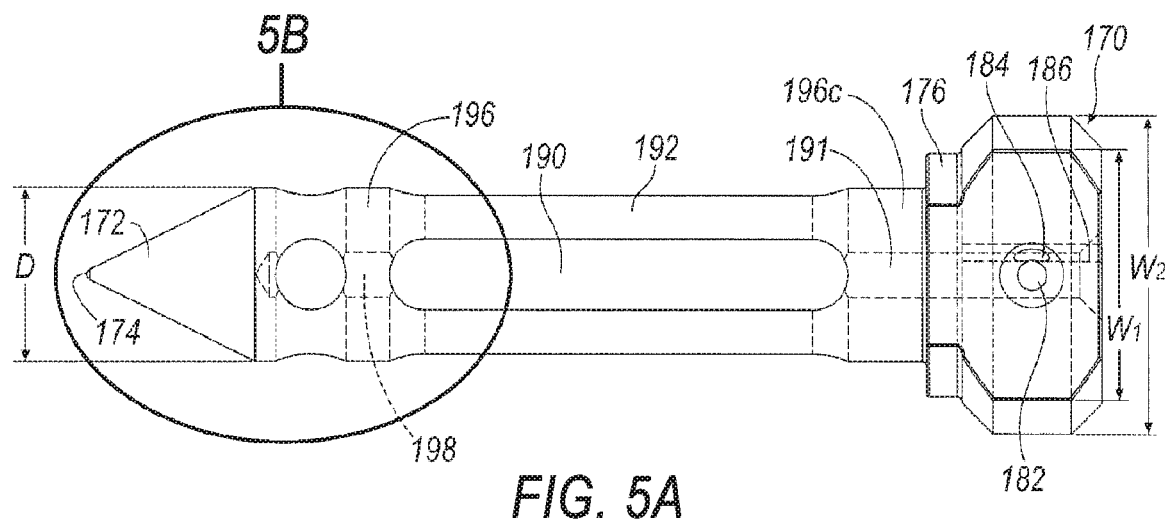
FIG. 5A is a top view of the obturator assembly of FIG. 4A.
Figure 5B:
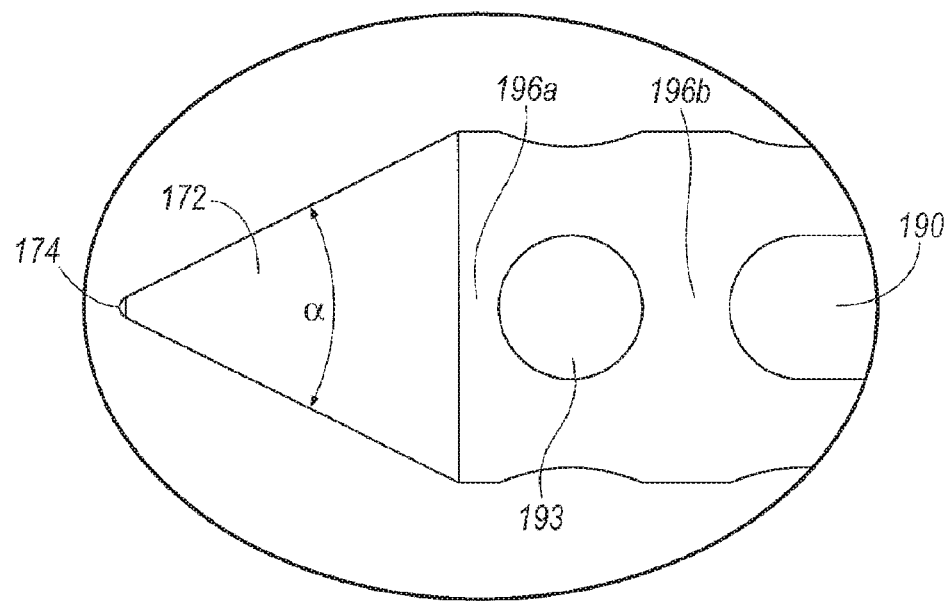
FIG. 5B is an enlarged view of a distal end of the obturator assembly taken from area 5B of FIG. 5A.
Figure 5C:
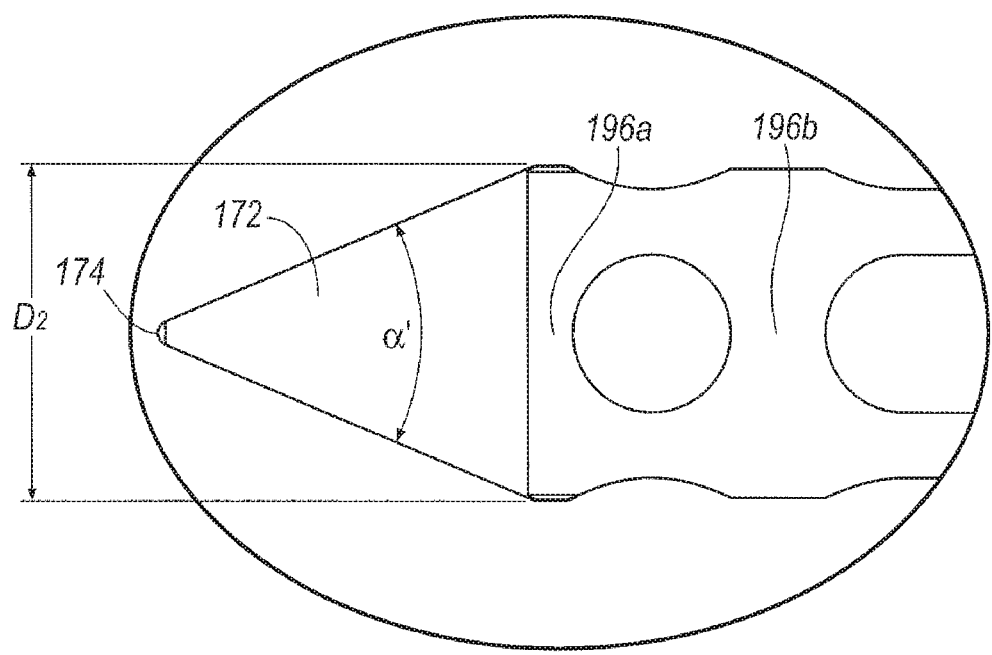
FIG. 5C is an alternative embodiment of the distal end of the obturator assembly taken from area 5B of FIG. 5A.

As best seen in FIG. 5B, distal tip 174 is configured to be radiused such that tip member 174 is rounded, and neither blunt, nor sharp. More specifically, tip member 174 is configured so as not to have any flat portions which during insertion can stretch or even tear the delicate tissues such as the vessels, fiber tracts and fascicles found in the brain. Further, because tip member 174 is closed, damage of such delicate tissues and fascicles are also avoided. In one exemplary embodiment, tip member 174 is configured with a 0.5 mm radius. As will be explained in further detail below, the configuration of tip member 174 is designed to gently displace and move the tissue into which it is inserted; i.e., atraumatically dilate the tissue to allow for introduction in to an intra-fascicular and para-fascicular manner, as opposed to cutting tissue as surgical access assembly 100 is inserted into the tissue.

Figure 4A:
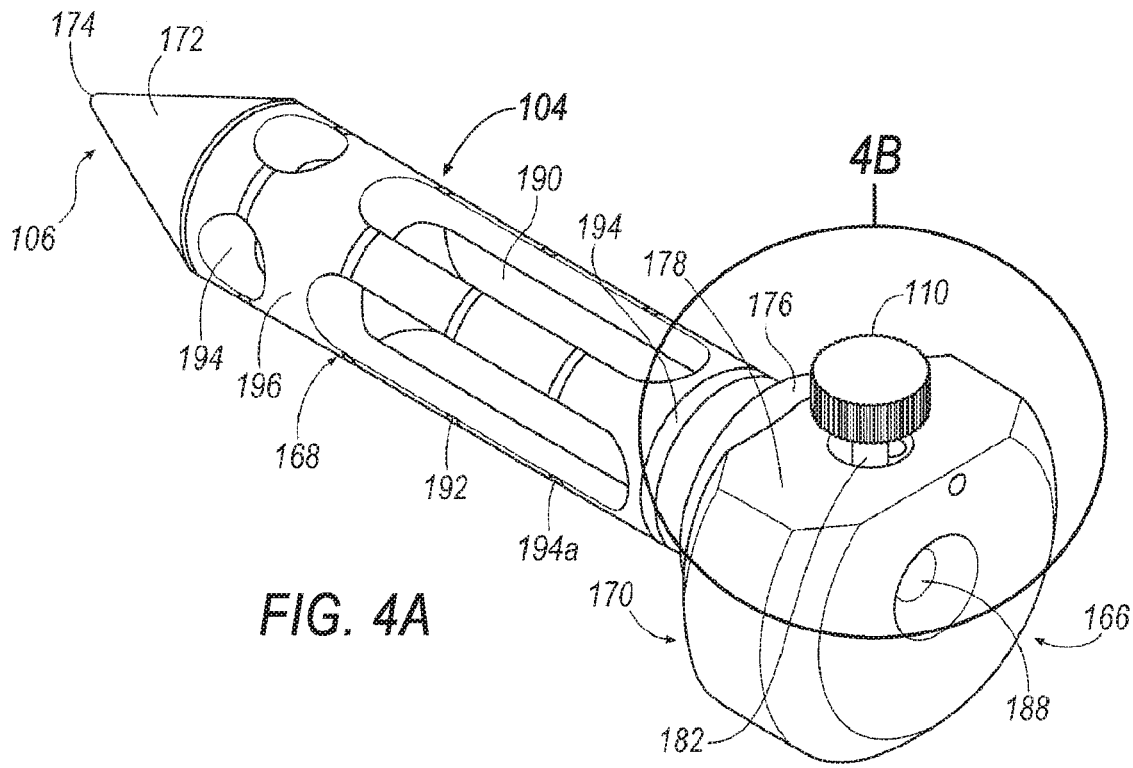
FIG. 4A is a perspective view of an obturator assembly of the surgical access assembly of FIG. 2.
Figure 6A:
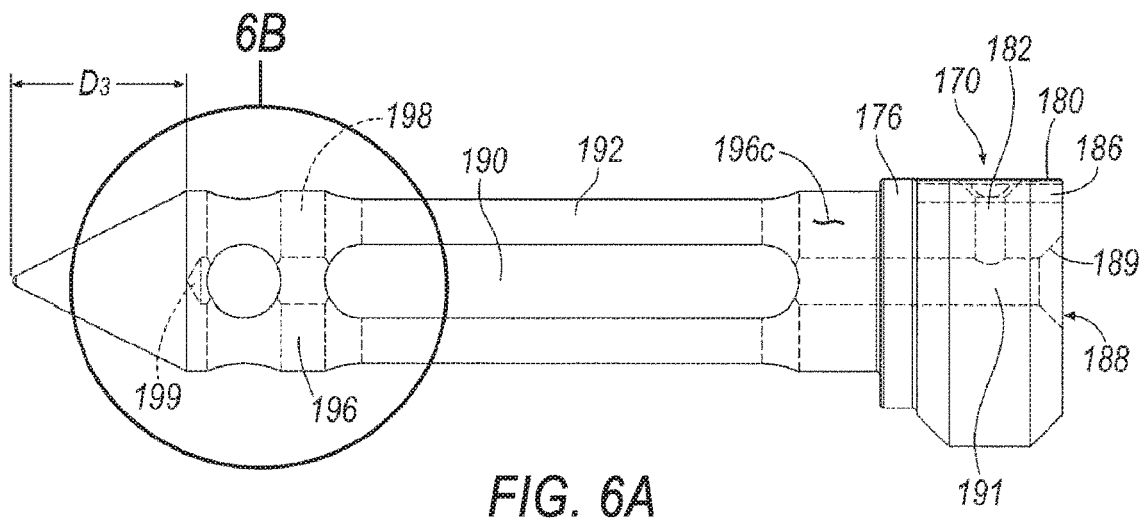
FIG. 6A is a side elevational view of the obturator assembly of FIG. 4A.

Handle portion 170 is positioned at proximal end 166 of obturator 104. As best seen in FIGS. 4A, 5A and 6A, handle portion 170 comprises a stop member 176 and a grip member 178. Stop member 176 is positioned distally of grip member 178 and, as best seen in FIG. 5A, is configured to have a width W1 that is greater than a diameter D1 of body portion 168, as well as a diameter D2 of outer sheath 102. Grip member 178 is configured with a width W2 that is greater than the width W1 of stop member 176, thereby providing a step-like configuration. Stop member 176 further defines an engagement surface 177 that is axially spaced from a distal surface 179 of grip member 178.

Figure 4B:
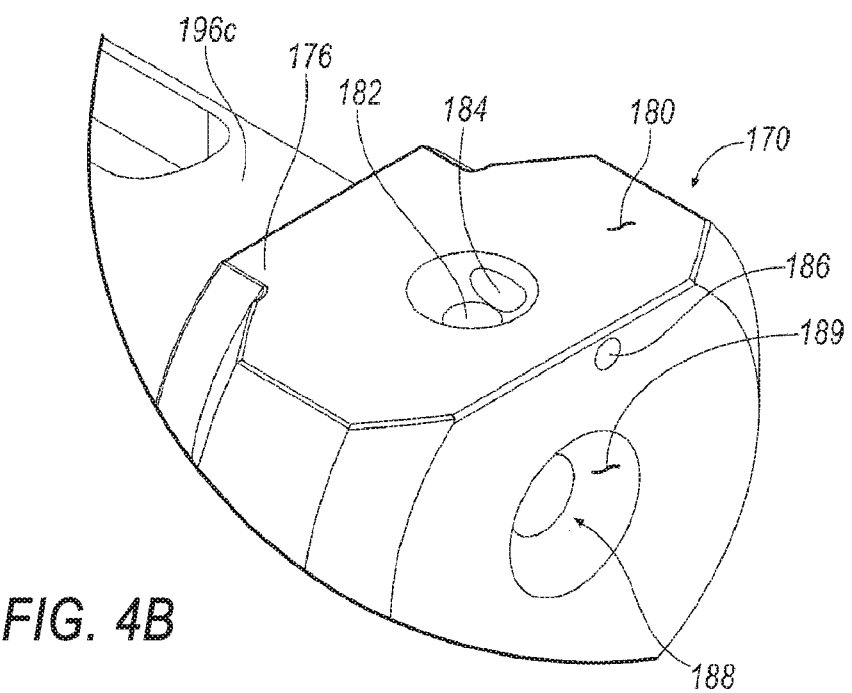
FIG. 4B is an enlarged view of an end face of the obturator assembly taken from area 4B of FIG. 4A.
Figure 6B:
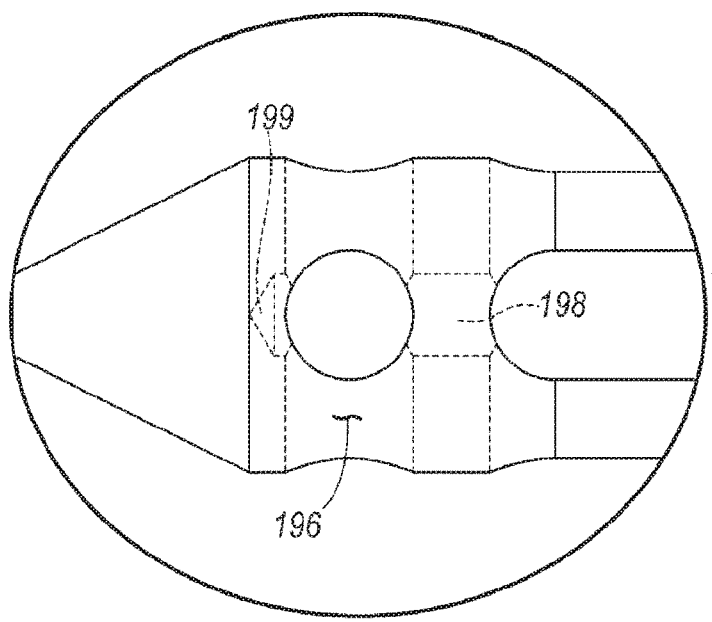
FIG. 6B is an enlarged view of a portion of the obturator assembly taken from area 6B of FIG. 6A.
Figure 6C:
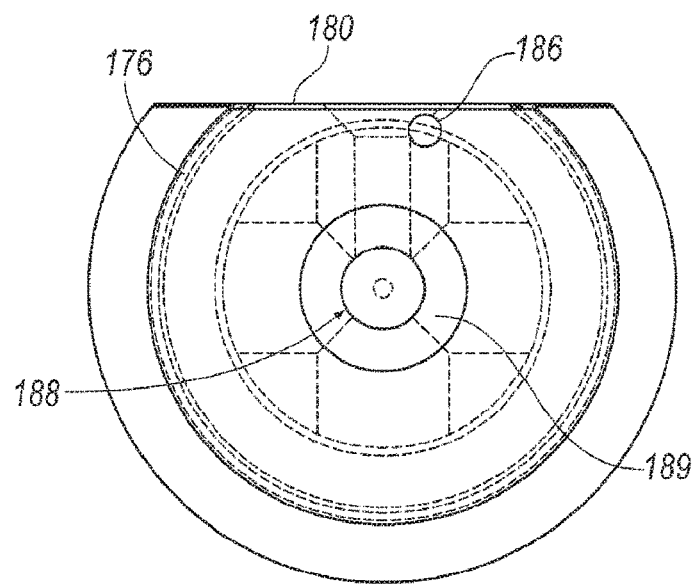
FIG. 6C is an end view of the obturator assembly of FIG. 4A.

In one exemplary arrangement, handle portion 170 is configured with a generally planar surface 180, as best seen in FIGS. 4A-4B and FIG. 6C. Planar surface 180 is configured with a receiving aperture 182 that is configured to receive locking member 110. In one exemplary arrangement, receiving aperture 182 is threaded. As best seen in FIGS. 2, 4B, and 5A, disposed within receiving aperture 182 is an engagement opening 184. Engagement opening 184 is in communication with a channel 186 (seen in phantom in FIGS. 5A and 6A) that extends at least partially thorough handle portion 170. After locking member 110 is at least partially engaged within receiving aperture 182, retaining member 114 (FIG. 2) is positioned within channel 186. Because engagement opening 184 opens into receiving aperture 182, a portion of retaining member 114 extends across a portion of receiving aperture 182 such that locking member 110 is prevented from being entirely withdrawn from receiving aperture 182. For example, locking member 110 is illustrated as having threads that cooperate with corresponding internal threads in receiving aperture 182. Retaining member 114 is positioned within channel 186 so as to extend above the threads of locking member 110 such as locking member 110 is being removed from receiving aperture 182, threads come into contact retaining member 114, thereby preventing complete removal of locking member 110 from handle portion 170.

An access opening 188 is formed through proximal end 166. Access opening 188 extends through handle portion 170. In one exemplary arrangement, access opening 188 may be provided with an inwardly extending chamfer 189 that tapers toward access opening 188. Chamfer 189 provides a self-directing feature for inserting navigation member 112 into access opening 188. Access opening 188 is in communication with a first channel segment 191 that extends through handle portion 170 and into body portion 168.

Body portion 168 extends between distal end 106 and proximal end 166. Body portion 168 includes one or more elongated void areas 190. Void areas 190 serve to reduce weight of obturator 104, thereby making obturator 104 easier to manipulate during surgical procedures. Void areas 190 also facilitate sterilization of obturator 104 by preventing moisture retention within body portion 168 of obturator 104. Further, void areas 190 also provide venting, thereby preventing a vacuum from being generated as obturator 104 is being withdrawn from outer sheath 102 during operation.

Void areas 190 are separated by web portions 192 that extend axially through a portion of the length of body portion 168. Disposed on web portions 192 of body portion 168 are one or more indicators 194 that may be read by an imaging system. Indicators 194 may include spaced apart hash marks (designated as 194A) that cooperate with an imaging modality to provide information, in real-time, concerning the location of obturator 104 relative to various tissue, critical structures, and fascicles within the brain, while obturator 104 is positioned within tissue. Indicators 194 also assist with providing information to regarding the relative positions between obturator 104 and outer sheath 102. For example, indicators 194 produce a signal void or minimal artifact under certain imaging modalities.

Body portion 168 may further include one or more cross webs 196. Cross webs 196 are oriented transverse to web portions 192 and connect web portions 192 together. In one exemplary arrangement, body portion 168 includes at least one cross web 196 that operatively defines the outer diameter D2 of body portion 168. Diameter D2 is sized to fit within lumen 148 of outer sheath 102 such that obturator 104 and outer sheath 102 may be selectively slid relative to one another. However, diameter D2 is also sized to minimize or even eliminate any gaps between an inner surface of outer sheath 102 and an outer surface of obturator 104. In the exemplary arrangement shown in FIG. 4-6, three cross webs 196A, 196B and 196C are provided. A first cross web 196A is connected to distal tip portion 172, while second cross web 196B is spaced proximally from first cross web 196A and separated by a void area 193. Third cross web 196C is separated from second cross web 196B by void areas 192 and is positioned distal from first stop member 176 of handle portion 170. Cross webs 196 serve to provide for structural integrity of obturator 104, as well as improved rigidity.

In one embodiment, cross web 196B is provided with a second channel segment 198 (shown in phantom) that extends there through. Second channel segment 198 is axially aligned with first channel segment 191 and is configured to selectively receive a portion of navigation member 112. In one exemplary arrangement, disposed in first cross web 196A is an inwardly extending depression 199, as best seen in FIG. 6B. Depression 199 is configured in such a manner so as to align a distal tip of navigation member 112 with distal end 108 of outer sheath 102, when outer sheath 102 is assembled to obturator 104 in the introducing configuration depicted in FIG. 2.

Referring to FIGS. 7-11, a first embodiment of a navigation member 112 that is part of a navigation stylet assembly 200 is illustrated. Navigation stylet 200 comprises navigation member 112, a handle 202, and attachment element 204 for a navigation array. The navigation member 112 includes a first navigation member portion 112a and a second navigation member portion 112b. Navigation member 112 is defined by distal and proximal ends 206, 208, respectively.

In one exemplary arrangement, the handle 202 may have an ergonomic shape. For example, in one exemplary arrangement, the handle 202 is configured with end members 212A, 212B, joined with a central land member 214. To reduce weight (i.e., by reducing material) of the handle 202, cutouts 216 may be provided. Cutouts 216 may also serve as finger grips. While shown with a teardrop shape, it is understood that cutouts 216 may have any shape.

Figure 11:
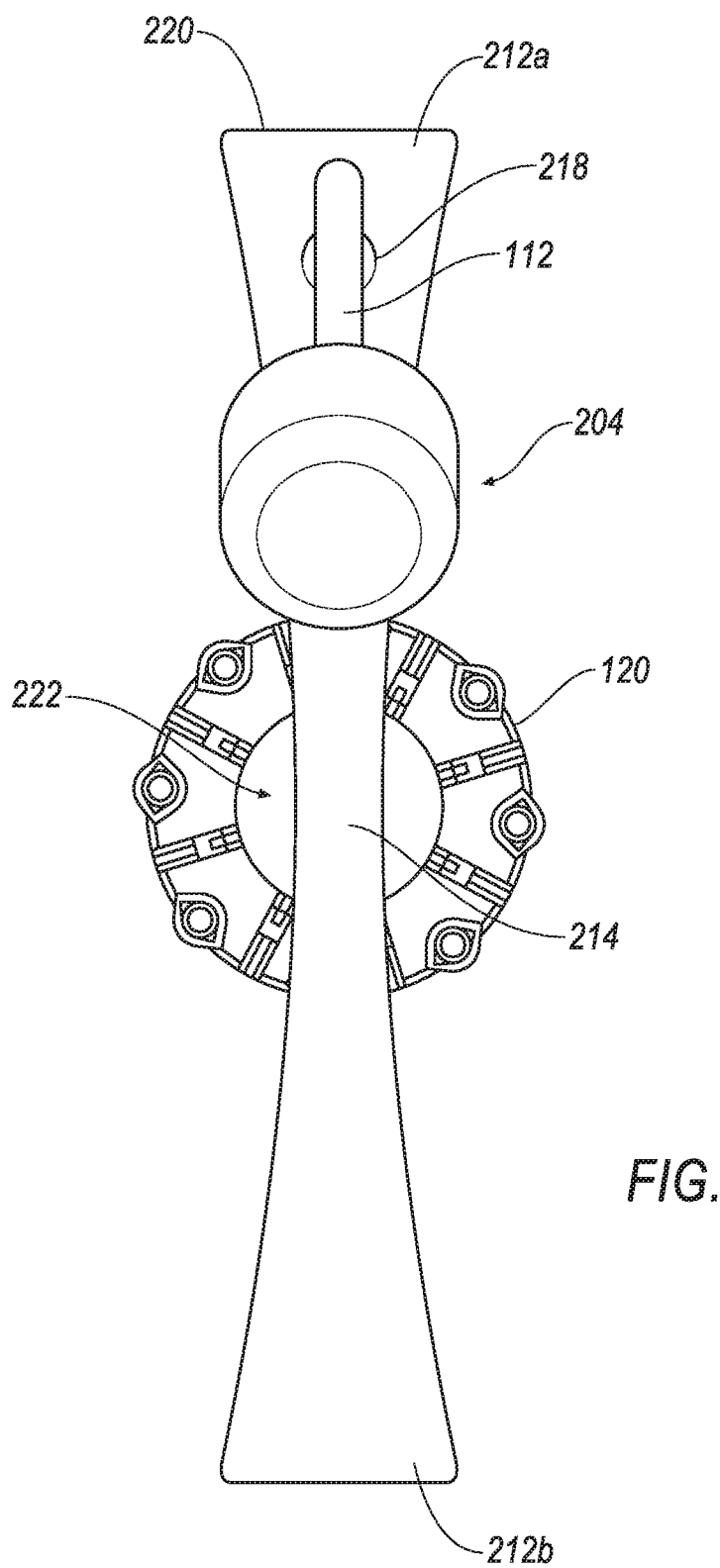
FIG. 11 is a top plan view of a portion of the navigation stylet of FIG. 7, while assembled to the surgical access system of FIG. 8.

The first navigation member portion 112a extends into the handle 202 (shown in phantom in FIG. 8) and the second navigation member portion 112b extends out of an opening 218 disposed in a top surface 220 of one of the end members 212A of the handle 202. A body element 210 of the navigation member 112 is defined between the distal end 206 and the handle 202. The navigation member 112 exits the opening 218 at a first trajectory $T_1$ extending away from the central land member 214. The navigation member 112 then bends at a bend point B such that the navigation member 112 extends back toward the central land member 214 along a second trajectory $T_2$. In one exemplary arrangement, the second trajectory $T_2$ is disposed 90° from the first trajectory $T_1$. The attachment element 204 for a navigation array (not shown) is attached to the proximal end 208 of the navigation member 112. The navigation array may be integrated to the attachment element 204 or removably attached. With this arrangement, the navigation array, when attached to the attachment element 204, will not completely obstruct the opening 222 (as shown in FIG. 11) through the grip ring 120 of the outer sheath 102. Indeed, this "forward" facing angle of the proximal end 208 of the navigation member 112 (and the attachment element 204) allows for the navigation array to be positioned out of the way of an external imaging and light delivery platform/technology, but still allows for detection by the navigation system.

To further facilitate visualization through the opening 222, the central land member 214 may be thinner than the end members 212A and 212B, as shown in FIG. 11. More specifically, the handle 202 may have a scalloped or hourglass shape (when viewed in plan view) that tapers inwardly toward the central land member 214 from each of the end members 212A and 212B. With this shape, direct visualization by a surgeon or through a scope in a surgical corridor created by the outer sheath 102 during an intraoperative navigation is available.

Referring to FIGS. 12-15, an alternative arrangement of a first embodiment of a navigation member 112 that is part of a navigation stylet assembly 300 is illustrated. Navigation stylet assembly 300 comprises navigation member 112, a handle 302, and attachment element 304 for a navigation array. The navigation member 112 is defined by distal and proximal ends 306, 308, respectively. A body element 310 extends between distal and proximal ends 306, 308.

In one exemplary arrangement, the handle 302 may have an ergonomic shape. In one exemplary arrangement, the handle 302 is configured with finger groove 312 disposed on one surface 313 of the handle 302. The surface 313, opposite of finger groove 312 may include inwardly extending posts 315 for positioning a portion of the body element 310 of the navigation member 112, as will be explained in further detail below. A side surface 317 of the handle 302 further includes a pair of openings 318A, 318B through which a portion of the navigation member 112 enters and exits the handle 302.

Figure 12:
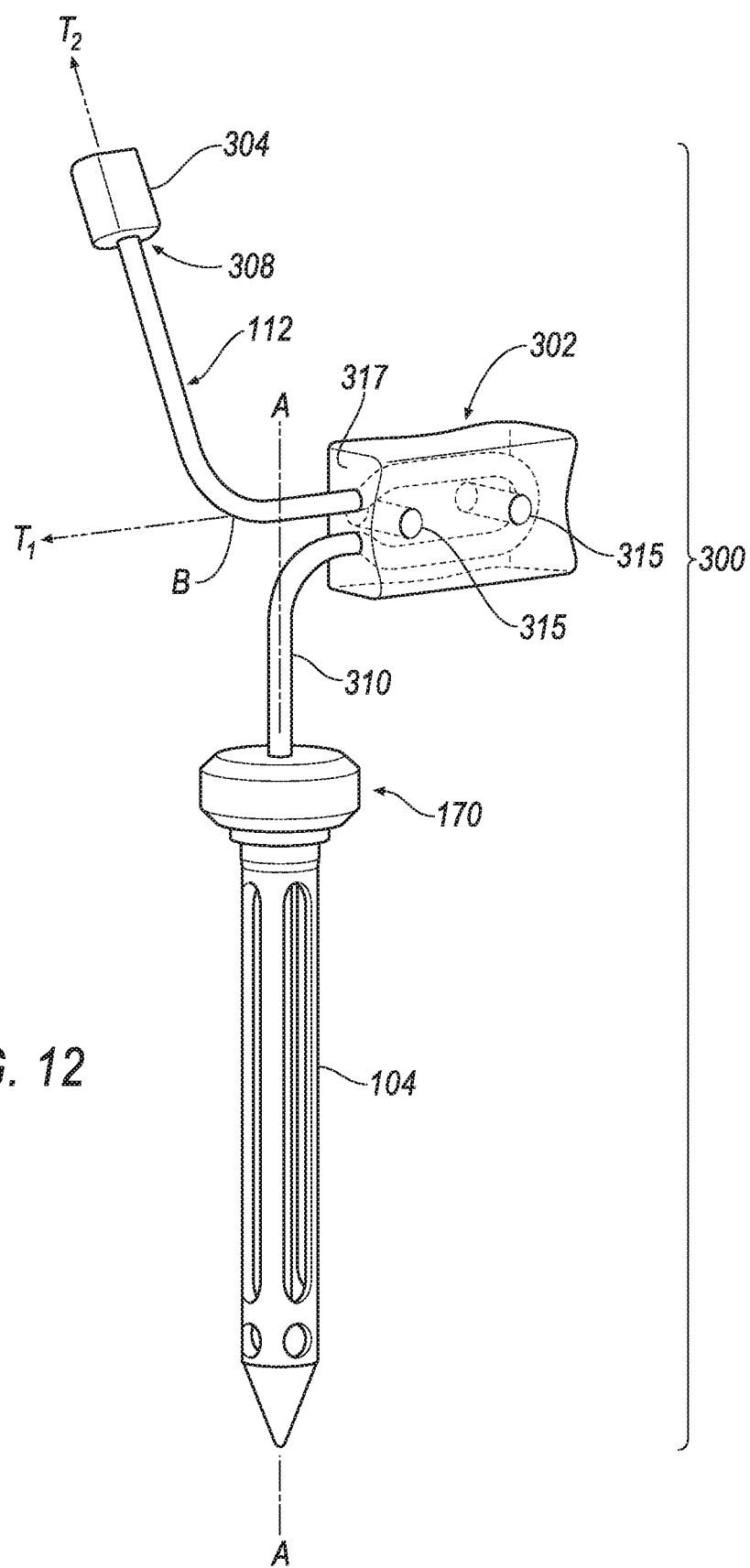
FIG. 12 is a side elevational view of an alternative embodiment of a navigation stylet for use with an obturator element of a surgical access system.
Figure 13:
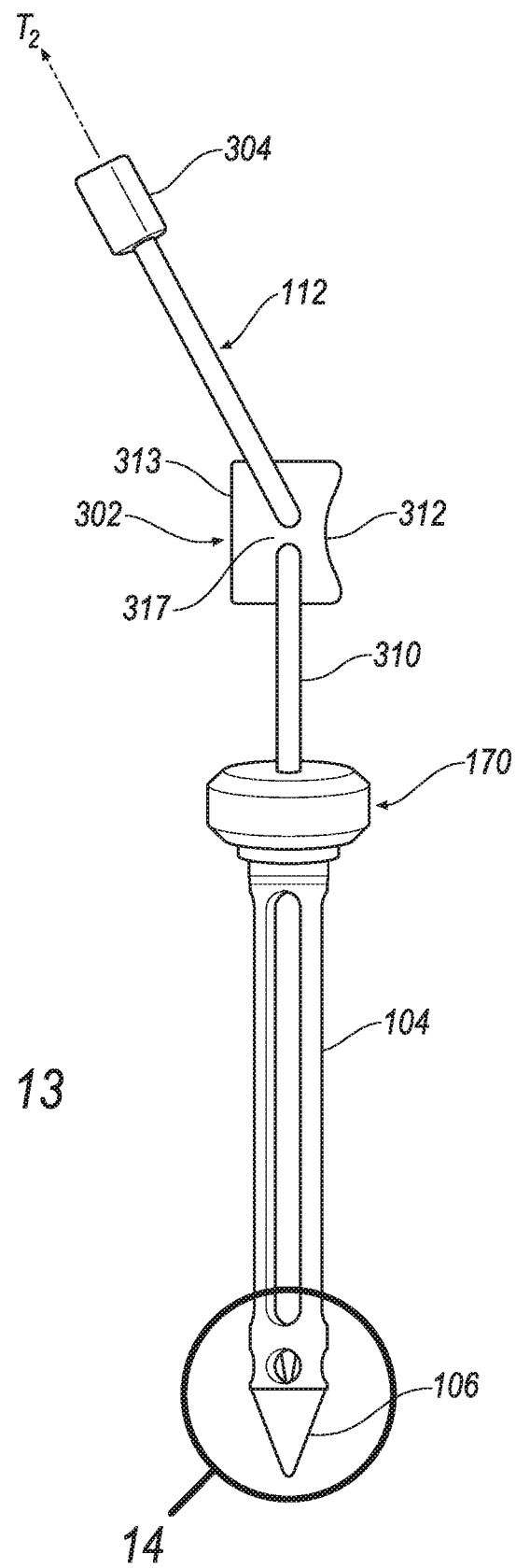
FIG. 13 is a side elevational view of the navigation stylet of FIG. 12.
Figure 14:
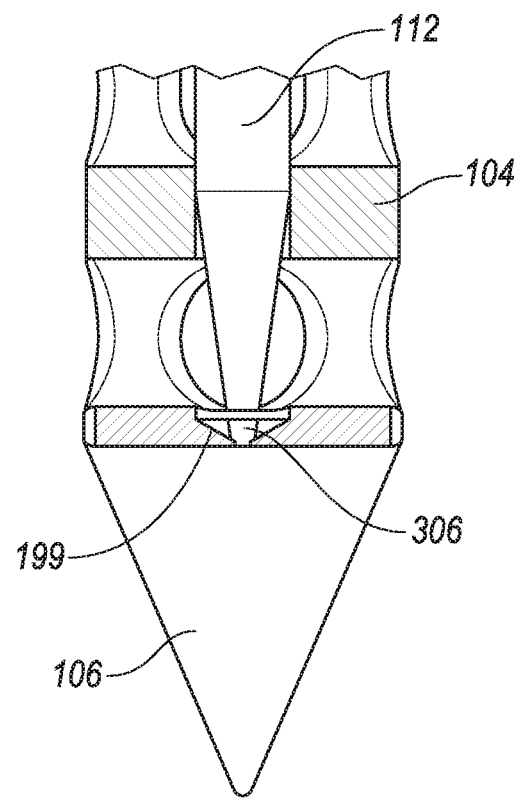
FIG. 14 is an enlarged view of a distal end of the navigation stylet seated in the introducer element taken from encircled area 14 of FIG. 13.
Figure 15:
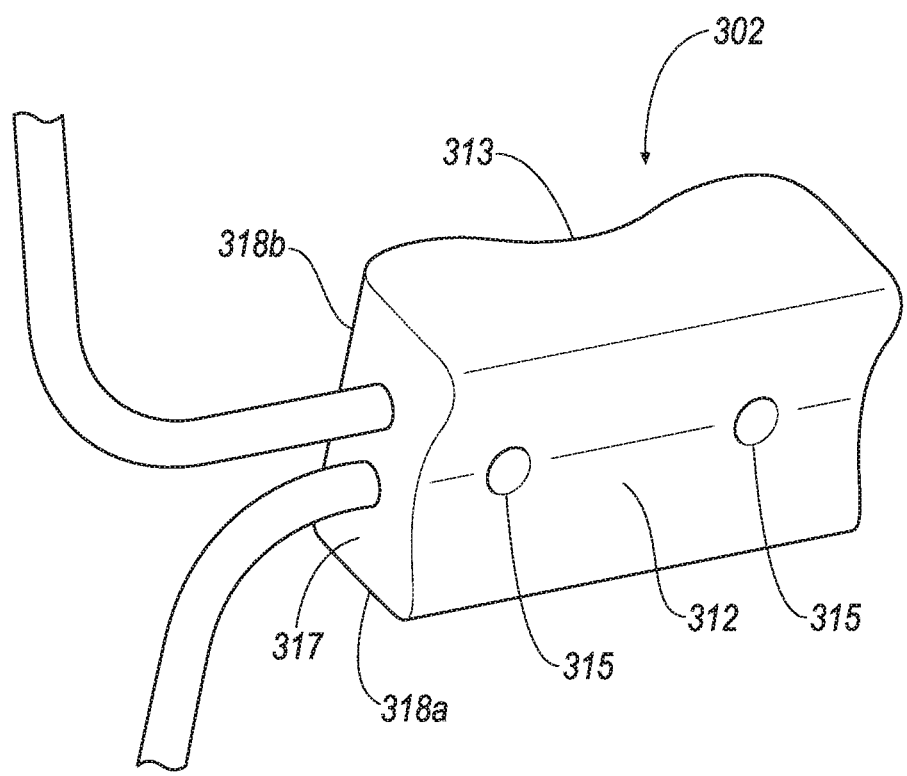
FIG. 15 is an enlarged view of a grip member of the navigation stylet.

As shown best in FIG. 12, the navigation member 112 extends into opening 318A of the handle 302 and is disposed around posts 315 so as to wrap around the posts 315 to change direction of the navigation member 112, as shown in FIG. 12. The navigation member 112 exits the handle 302 at opening 318B. As may be seen in FIG. 12, the handle 302 is configured to be positioned to a side of the obturator 104 so as not to impede visualization of the surgical access assembly 100. When exiting the handle 302, the navigation member 112 initially proceeds along a first trajectory $T_1$ extending laterally away from the handle 302. The navigation member 112 then bends at a bend point B such that the navigation member 112 extends upwardly, but still being angled away from a central axis A-A that extends through the obturator 104, along a second trajectory $T_2$ (best shown in FIG. 13). The attachment element 304 for a navigation array (not shown) is attached to the proximal end 308 of the navigation member 112. The navigation array may be integrated to the attachment element 304 or removably attached. The navigation array, when attached to the attachment element 304 will not completely obstruct the opening through the grip ring 120 (shown in FIG. 3) of the outer sheath 102. The angled proximal end 308 of the navigation member 112 (and the attachment element 304) allows for the navigation array to be positioned out of the way of an external imaging and light delivery platform/technology, as well as being detectable by the navigation system.

Figure 16:
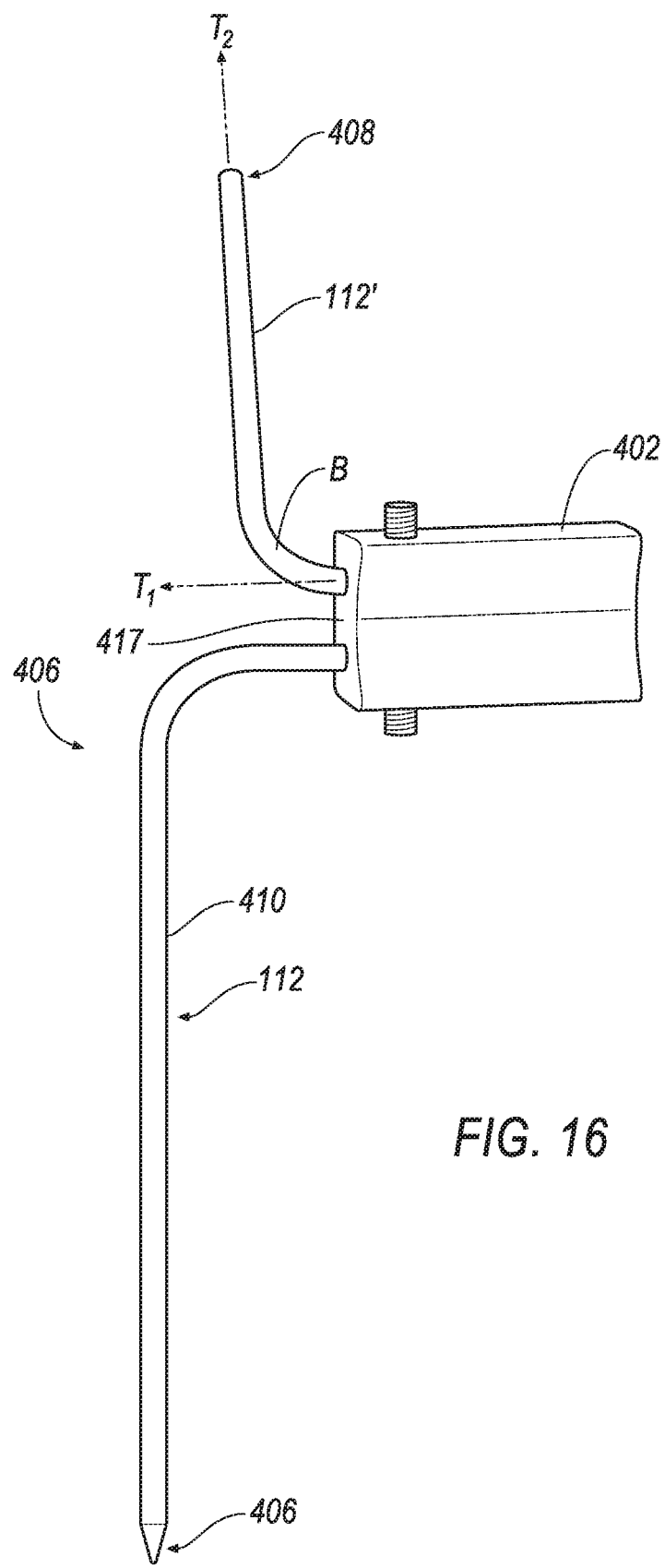
FIG. 16 is an elevational view of an alternative arrangement of the navigation stylet of FIG. 11.
Figure 17:
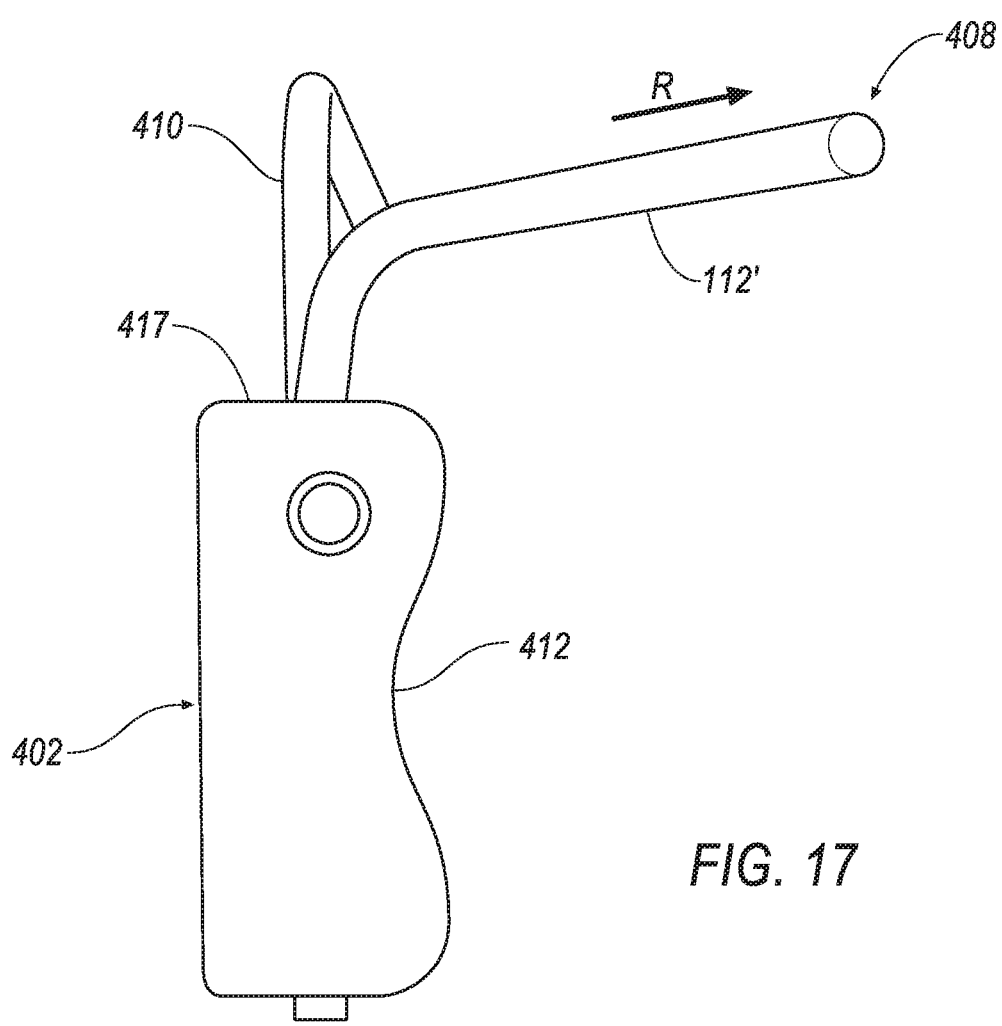
FIG. 17 is a top plan view of the navigation stylet of FIG. 16.

Referring to FIGS. 16-17, an alternative arrangement of navigation stylet assembly 400 is illustrated. Navigation stylet assembly 400 is generally configured the same as navigation stylet assembly 300 in that the navigation stylet assembly 400 comprises navigation member 112, a handle 402, and may include an attachment element (not shown) for a navigation array. The navigation member 112 is defined by distal and proximal ends 406, 408, respectively. A body element 410 extends between distal and proximal ends 406, 408.

The handle 402 may be configured similar to the handle 302, including having a finger groove 412 disposed on one surface of the handle 402, and the inwardly extending posts (not shown) for angling a portion of the body element 410 of the navigation member 112. A side surface 417 of the handle 402 further includes a pair of openings through which a portion of the navigation member 112 enters and exits the handle 402.

The navigation member 112 extends into one of the openings of the handle 402 and is disposed within the handle 402. A proximal end section 112' of the navigation member 112 exits the handle 402 at the other opening. As may be seen in FIG. 16, the handle 402 is positioned to a side of the body element 410. When exiting the handle 402, the proximal end section 112' of the navigation member 112 proceeds along a first trajectory $T_1$ extending laterally away from the handle 402. The navigation member 112 then bends at a bend point B such that the navigation member 112 extends upwardly, along a second trajectory $T_2$. In the navigation stylet assembly 400, the proximal end section 112' is disposed closer to handle 402 than body element 410. As illustrated in FIG. 17, the second trajectory $T_2$ may extend in a rearward direction R with respect to the handle. The attachment element for a navigation array (not shown) may be attached to the proximal end 408 of the navigation member 112. The navigation array may be integrated to the attachment element 304 or removably attached. The navigation array, when attached to the attachment element, will not completely obstruct the opening through the grip ring 120 (shown in FIG. 3) of the outer sheath 102. The angled proximal end 408 of the navigation member 112 (and the attachment element) allows for the navigation array to be positioned out of the way of an external imaging and light delivery platform/technology, as well as being detectable by the navigation system.

For all embodiments of the navigation member 112, when the navigation stylet assemblies 200, 300, 400 are assembled with the obturator 104, the distal end 206/306/406 of the navigation member 112 is disposed within the inwardly extending depression 199 of the obturator 104. As explained above, depression 199 is configured in such a manner so as to align a distal tip of navigation member 112 with distal end 108 of outer sheath 102, when outer sheath 102 is assembled to obturator 104 in the introducing configuration. With this arrangement, the location of the distal tip 106 of the obturator 104 may be easily determined.

For all embodiments of the navigation member 112, the navigation stylet assemblies 200, 300, 400 may be configured to be selectively adjustable. More specifically, the stylet 112 and/or the proximal end section 112' may be selectively pivotable or bendable with respect to the handle 402.

With regard to the processes, systems, methods, heuristics, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of processes herein are provided for the purpose of illustrating certain embodiments, and should in no way be construed so as to limit the claims.

Accordingly, it is to be understood that the above description is intended to be illustrative and not restrictive. Many embodiments and applications other than the examples provided would be apparent upon reading the above description. The scope should be determined, not with reference to the above description, but should instead be determined with reference to the appended claims, along with the full scope of equivalents to which such claims are entitled. It is anticipated and intended that future developments will occur in the technologies discussed herein, and that the disclosed systems and methods will be incorporated into such future embodiments. In sum, it should be understood that the application is capable of modification and variation.

All terms used in the claims are intended to be given their broadest reasonable constructions and their ordinary meanings as understood by those knowledgeable in the technologies described herein unless an explicit indication to the contrary in made herein. In particular, use of the singular articles such as "a," "the," "said," etc. should be read to recite one or more of the indicated elements unless a claim recites an explicit limitation to the contrary.

What is claimed is:

1. A navigation stylet assembly, comprising:
   a navigation element;
   a handle attached to the navigation element; and
   an attachment member configured to be attached to a navigation array attached to a proximal end of the navigation element; wherein the navigation element includes a first portion and a second portion and wherein the first portion extends along a central axis disposed through a body element of the navigation element and wherein the second portion extends outwardly from the handle so as to be oriented at an angle that extends away the central axis.

2. The navigation stylet assembly of claim 1, wherein part of the navigation element is disposed within the handle.

3. The navigation stylet assembly of claim 2, wherein a proximal end of the navigation element exits the handle and extends along a first trajectory that is oriented away from the handle and the central axis.

4. The navigation stylet assembly of claim 3, further comprising a bend point in the navigation element, wherein the proximal end of the navigation element is directed along a second trajectory that is different than the first trajectory at the bend point.

5. The navigation stylet assembly of claim 4, wherein the second trajectory extends upwardly and at an angle from the first trajectory.

6. The navigation stylet assembly of claim 5, wherein the second trajectory is disposed 90° from the first trajectory.

7. The navigation stylet assembly of claim 5, wherein the second trajectory extends in a rearward direction with respect to the handle.

8. The navigation stylet assembly of claim 2, wherein the handle further comprises at least one support post disposed therein, and wherein the navigation element is disposed around the support post within the handle.

9. The navigation stylet assembly of claim 8, wherein the handle further comprises a finger groove.

10. The navigation stylet assembly of claim 8, wherein a side of the handle includes a pair of openings, wherein the body element of the navigation element enters one of the openings and the proximal end of the navigation element exits the handle at another of the openings.

11. The navigation stylet assembly of claim 2, wherein the handle is disposed so as to be offset from the central axis.

12. The navigation stylet assembly of claim 2, wherein the handle is defined by opposing ends and a central land member disposed between the opposing ends.

13. The navigation stylet assembly of claim 12, wherein the central land member has a width that is less than the width of the opposing ends.

14. The navigation stylet assembly of claim 12, wherein portions of the opposing ends further comprise cutouts.

15. The navigation stylet assembly of claim 1, wherein the proximal portion of the navigation element is positioned closer to the handle than the body element of the navigation element.

16. A surgical access system, comprising:
   an outer sheath defined by an open distal end and an open proximal end and including a hollow body portion therebetween;
   an obturator defined by a distal end and a proximal end, wherein the distal end further comprises a tapered distal tip member that terminates in a closed distal tip; and
   a navigation element configured to be selectively received and fixed to the obturator; wherein the navigation element is configured to indicate a location of the obturator within a patient during use; wherein the navigation element further comprises a handle attached to the navigation element; and an attachment member configured to be attached to a navigation array; wherein the navigation element includes a first portion and a second portion, wherein the first portion extends along a central axis disposed through the body element of the navigation element and the obturator, wherein the second portion of the navigation element is bent such that the second portion of the navigation element extends out of said handle and is oriented at an angle that extends away from a central axis disposed through a body element of the navigation element and the obturator.

17. The surgical access system of claim 16, further comprising a tracking marker assembly attached to the outer sheath.

18. The surgical access system of claim 16, wherein a proximal end of the navigation element exits the handle and extends along a first trajectory that is oriented away from the handle and the central axis, and further comprises a bend point, and wherein the proximal end of the navigation element directed along a second trajectory that is different than the first trajectory at the bend point.

19. The navigation stylet assembly of claim 18, wherein the second trajectory extends upwardly and at an angle from the first trajectory.

\* \* \* \* \*